US00PP12106P2

(12) United States Plant Patent
Hanes

(10) Patent No.: US PP12,106 P2
(45) Date of Patent: Sep. 25, 2001

(54) GERANIUM PLANT NAMED 'AMRI BRIGHT RED'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 0 days.

(21) Appl. No.: 09/335,184

(22) Filed: Jun. 17, 1999

(51) Int. Cl.[7] ..... A01H 5/00
(52) U.S. Cl. ..... Plt./330
(58) Field of Search ..... Plt./330, 324, 325

(56) References Cited

U.S. PATENT DOCUMENTS

P.P. 7,935 * 8/1992 Hanes ..... Plt./330

P.P. 10,399 * 5/1998 Trees ..... Plt./330

OTHER PUBLICATIONS

GTITM UPOVROM Citation for 'Amri Bright Red' as per QZ PBR 970752; Jun. 27, 1997.*

* cited by examiner

*Primary Examiner*—Bruce R. Campell
*Assistant Examiner*—Kent L. Bell
(74) *Attorney, Agent, or Firm*—Rothwell, Figg, Ernst & Manbeck

(57) ABSTRACT

A new and distinct geranium plant named 'Amri Bright Red' is provided. 'Amri Bright Red' is characterized by its green foliage, red colored semi-double flowers on large umbels, and early flowering.

1 Drawing Sheet

BACKGROUND OF THE NEW PLANT

The present invention comprises a new and distinct geranium plant, botanically known as *Pelargonium hortorum* Bailey, and hereinafter referred to by the name of 'Amri Bright Red'.

This new geranium originated from a cross made by the inventor of the seed parent 4163-1 (unpatented), a scarlet flowered plant from the breeding line 4163, and the pollen parent 3459-1 (unpatented), a red flowered plant from the breeding line 3459. The breeding line 3459 has the commercial variety 'Fox' (U.S. Plant Pat. No. 7,083) as it's pollen parent.

'Amri Bright Red' is the product of a planned breeding program intended to create new geranium plants with red colored flowers, semi-double flower form, green foliage, vigorous growth and superior cutting productivity.

'Amri Bright Red' was created in 1994 in Gilroy, Calif., and has been repeatedly asexually reproduced by cuttings in Gilroy, Calif., and Guatemala over a five-year period. The plant has also been trialed at Okemos, Mich. The plant has been found to retain its distinctive characteristics through successive propagations; and this novelty appears to be firmly fixed and reproduces true to the type.

DESCRIPTION OF THE DRAWING

This new geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVAR

Figure 1:
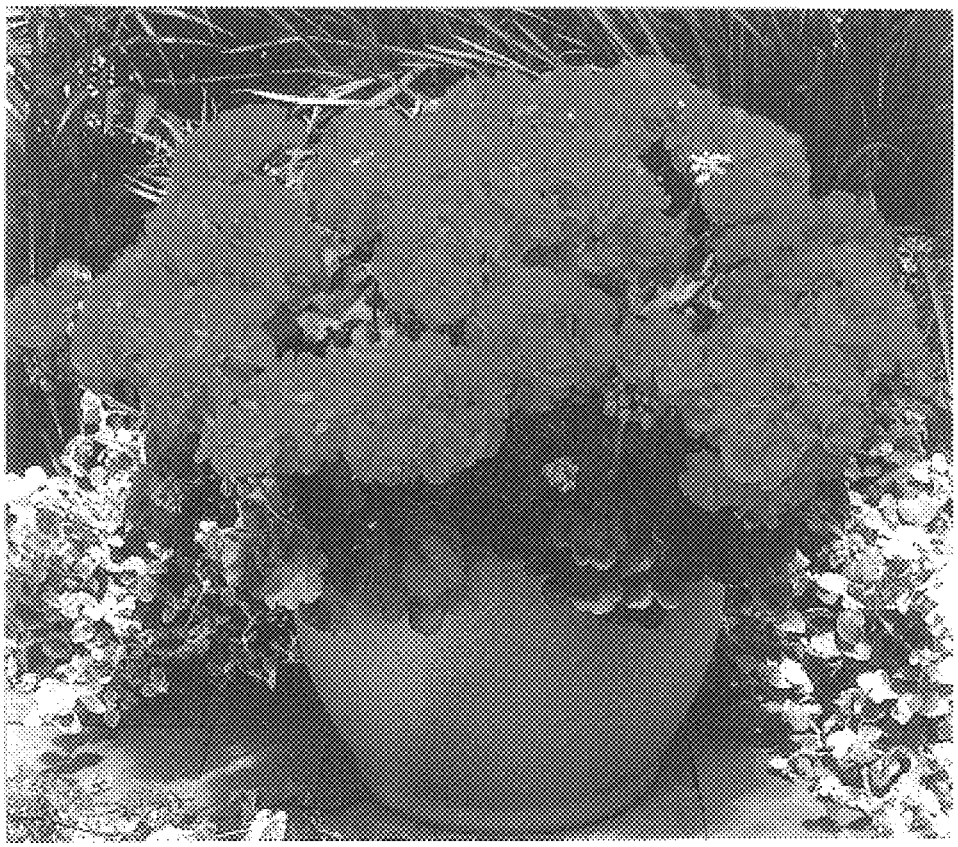
FIG. 1 shows the overall plant habit.

The following detailed descriptions set forth the distinctive characteristics of 'Amri Bright Red'. The data which defines these characteristics were collected from asexual reproductions carried out in Gilroy, Calif. The plant history was taken on 14 week old plants, blossomed under natural light in a greenhouse and color readings were taken in indirect sun light (shade), in Gilroy, Calif. Color references are primarily to The R.H.S. Colour Chart of The Royal Horticultural Society of London (R.H.S.).

The Plant

Classification:
- *Botanical.*—*Pelargonium hortorum* Bailey.
- *Commercial.*—Zonal geranium.

Form: Upright rounded plant.

Height: 12 cm., in a 4-inch pot plant, excluding blooms; plant height from soil level to top of umbels is 21–23 cm; width is 20–26 cm.

Growth: Vigorous, good basal branching, withstands multiple harvests of cuttings, produces a commercially acceptable size flowering plant in a 4 inch pot within 12 weeks and produces a strong, weather resistant plant in outdoor field trials in several different climate zones.

Plant habit: Early flowering. Good shipping ability as rooted or unrooted cuttings.

Time to produce a finished flowering plant: 12 weeks.

Outdoor plant performance: The plant exhibits good heat tolerance and strong growth, with a rounded habit.

Leaves:
- *Quality.*—Abundant.
- *Size.*—Diameter approximately 7.5 cm; Length is 4.2–4.7 cm; Apex is obtuse; Base is cordate.

*Shape.*—Rounded cordate with occasional up folding between veins.

*Margin.*—Irregularly crenate.

*Texture.*—Leathery and pubescent on both surfaces, especially along veins.

*Ribs and veins.*—Distinctly palmate, 3 to 4.5 cm long.

*Color.*—Upper side; green, RHS 146A, with leaf zone in central region approximately 1.0–1.5 cm and yellow-green RHS 147A. Under side: Lighter green, RHS 146B, in color. Ribs and veins not prominently different from upper surface.

*Petioles.*—Approximately 4.2 to 5.5 cm in length, diameter is 3 mm and color is yellow-green RHS 146A.

*Lateral branches.*—Length is 4–7 cm; Internode is 1–2 cm; Color is yellow-green RHS 144A.

*Roots.*—Time to initiate roots is 7–10 days; time to develop roots is 3–4 weeks; description is fibrous yet coarse, white, slightly hairy.

The Bud

Size:

*Diameter.*—Approximately 5 mm.

*Length.*—Approximately 2 cm. to 2.5 cm. at time of bud opening.

Shape: Pointed ovoid.

Color: Petals when sepals first divide, red RHS 45B.

Sepals: 5 in number, flat behind petals. Pointed linear lanceolate. Length is 1 cm; Width is 4 mm; Apex is acute; Base is truncate; Upper color is yellow-green RHS 144A; Lower color is yellow-green RHS 146B; upper and lower surfaces have a red-purple RHS 59B stripe at the base.

The Flower

Flowering season: Continuous throughout the year.

Size: Approximately 5.2 cm. diameter, 1.7 cm. deep, irregularly radially symmetrical.

Form: Cup-shaped semi-double flowers when bloom first opens, later flattening to shallow cup shaped semi-double flowers with maturity.

Petals/petaloids: Six to eight imbricate petals, spatulate shaped 2.6–2.8 cm wide and approximately 2.7 cm long, retuse apex, attenuate base and entire margins. Two to three petaloids of varying shape. Both petals and petaloids upper surface color is red, RHS 46B and lower surface of petals and petaloids is red RHS 44B. Petals and petaloids darken over time to red RHS 46A. Petals and petaloids soft and satiny.

Pedicel: Approximately 2.3 cm. in length; yellow-green RHS 145A with red-purple RHS 59B on top third of the pedicel where it meets the sepals.

Persistence: An open flower will hold its petals until the flower begins to dehisce or approximately 7–10 days.

Inflorescence

Type: An umbel composed of approximately 25 flowers, erect or laterally ascending; diameter is 9–11 cm; depth is 5–5.5 cm from bottom of pedicel to top of umbel.

Peduncle: Approximately 13–18 cm. in length, green, RHS 146B near the base fading to 146C near the top where the buds are located, with red tint, RHS 59A, on the sun exposed side.

Reproductive Organs

Stamens:

*Anthers.*—8–10 positioned below the mature stigma, dull red, RHS 50B, prior to anthesis.

*Filaments.*—White near base and mid length, graduating to dull red, RHS 61B, near anther.

*Pollen.*—Moderate amount; Orange, RHS 32A, in color.

Pistil:

*Number.*—1.

*Length.*—Approximately 3 mm.

*Stigma.*—5 linear lobes of near equal length, curling back toward ovary, purplish-red RHS 53B.

*Style.*—Length: Approximately 8 mm., color: Purplish red RHS 53A.

*Ovaries.*—At anthesis, densely pubescent with white hairs, oblong. Green drying to a light brown at maturity.

Fruit/seeds: Partially fertile; maximum of five seeds per seed spike; seed length is approximately 4 mm; width is 1 mm; color is grey-orange RHS 177B but may darken with age.

Disease/Insect Resistance

No known susceptibility or resistance to typical diseases and insects of geraniums.

Comparison with Parental Cultivars

'Amri Bright Red' has a semi-double flower form as compared to a single flower form for the parental cultivar 4163-1. Additionally, 4163-1 has a more orange-scarlet flower color than 'Amri Bright Red'. The other parental cultivar, 3459-1, has a darker red flower color than the present invention and also has darker green foliage.

I claim:

1. A new and distinct geranium plant substantially as herein shown and described, named 'Amri Bright Red', that is characterized by green foliage with red colored semi-double flowers on large umbels, and early flowering.

* * * * *